United States Patent [19]

Beaton et al.

[11] E Patent Number: Re. 33,364

[45] Reissued Date of Patent: Oct. 2, 1990

[54] NON-AROMATIC OXYGENATED STRONG ACID DEHYDRATION OF 9α-HYDROXYANDROSTENEDIONES

[75] Inventors: John M. Beaton, Portage; Joel E. Huber, Kalamazoo; Amphlett G. Padilla; Max E. Breuer, both of Portage, all of Mich.

[73] Assignee: The Upjohn Company, Kalamazoo, Mich.

[21] Appl. No.: 181,752

[22] Filed: Apr. 14, 1988

Related U.S. Patent Documents

Reissue of:

[64] Patent No.: 4,127,596
Issued: Nov. 28, 1978
Appl. No.: 786,127
Filed: Apr. 11, 1977

[51] Int. Cl.[5] ..... C07J 1/00

[52] U.S. Cl. ..... 552/640

[58] Field of Search ..... 260/397.3, 397.45

[56] References Cited

U.S. PATENT DOCUMENTS 4,029,648 6/1977 Ponsold et al. ..... 260/397.45

*Primary Examiner*—Joseph A. Lipovsky
*Attorney, Agent, or Firm*—Bruce Stein

[57] ABSTRACT

The present invention discloses a process for the production of androsta-4,9(11)-diene-3,17-dione type compounds from 9α-hydroxyandrostenedione type compounds by non-aromatic oxygenated strong acid dehydration.

23 Claims, No Drawings

NON-AROMATIC OXYGENATED STRONG ACID DEHYDRATION OF 9α-HYDROXYANDROSTENEDIONES

Matter enclosed in heavy brackets [ ] appears in the original patent but forms no part of this reissue specification; matter printed in italics indicates the additions made by reissue.

BACKGROUND OF THE INVENTION

Androstenedione is a $C_{19}$ steroid of the formula:

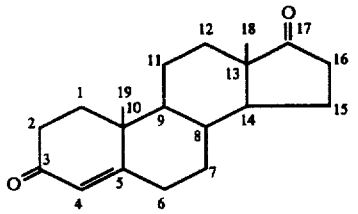

Androsta-4,9(11)-diene-3,17-dione refers to androstenedione with an additional double bond between carbon atoms 9 and 11. Androsta-4,9(11)-diene-3,17-dione type compounds refer to steroids within the scope of formula II:

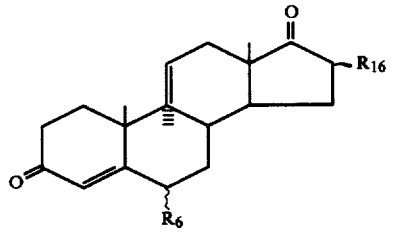

II $R_6$, $R_{16}$ and ~ are defined infra.

The androsta-4,9(11)-diene-3,17-dione type compounds (II) are useful for producing pharmaceuticals, in particular testosterone derivatives. For example, androsta-4,9(11)-diene-3,17-dione (II) is converted to 3-(N-pyrrolidinyl)-androsta-3,5,9(11)-triene-17-one to protect the $C_3$ ketone by the process disclosed by F. W. Heyl and M. E. Herr in J. Am. Chem. Soc. 77, 488 (1955). This protected steroid is converted to 17β-hydroxy-17α-methylandrosta-4,9(11)-diene-3-one by a Grignard reaction with methyl magnesium bromide and subsequent alkaline hydrolysis. See M. E. Herr et al., J. Am. Chem. Soc. 78, 500 (1956). This methyltestosterone derivative is then converted to 9α-fluoro-11β,17β-dihydroxy-17-methylandrost-4-en-3-one (fluoxymesterone, Halotestin ®) which is a commercially marketed steroid, by the process of U.S. Pat. No. 3,118,880, Example 2.

The $\Delta^{9(11)}$-steroids have been prepared from both 11β-hydroxy steroids and 9α-hydroxy steroids. George G. Hazen and D. W. Rosenburg, J. Org. Chem. 29, 1930(1964) and U.S. Pat. No. 3,094,543; D. Taub et al., J. Am. Chem. Soc. 82, 4102 (1970); E. M. Chamberlain, J. Org. Chem. 25, 295 (1960); T. Reichstein, U.S. Pat. No. 2,409,798; Drake, U.S. Pat. No. 3,005,834; and Great Britain Pat. No. 1,198,749 all disclose synthesis of $\Delta^{9(11)}$, steroids from 11β-hydroxy steroids. The papers and patents by Hazen, Taub, and Chamberlain all disclose using 11β-hydroxy corticoids to form the corresponding $\Delta^{9(11)}$-corticoids. U.S. Pat. No. 2,409,798 (Example 3), U.S. Pat. No. 3,005,834 (Example 35) and Great Britain Pat. No. 1,198,749 (Example 1) disclose the use of 11β-hydroxyandrostenes to produce $\Delta^{9(11)}$-androstenes.

The $\Delta^{9(11)}$-steroids have also been prepared from the corresponding 9α-hydroxy steroids.

East German Pat. No. 20,528 disclosed using p-TSA in dry benzene to dehydrate 9α-hydroxy steroids of the pregnane series to the corresponding $\Delta^{9(11)}$-pregnanes, C. G. Bergstrom and R. B. Dodson, Chem. and Ind. (London) 1530 (1961), treated 9α-hydroxyandrostenedione with p-TSA in benzene. Upon workup 9,10-secoandrost-4-ene-3,9,17-trione and 9α-hydroxy-4-methylestr-4-ene-1,17-dione were identified; there was no androsta-4,9(11)-diene-3,17-dione (II).

C. G. Bergstrom et al. in J. Org. Chem. 28, 2633 (1963) at page 2638 described reacting 2.0 g. of 9α-hydroxyandrostenedione with hydrogen fluoride pyridine reagent to produce 9α-fluoroandrostenedione as well as androsta-4,9(11)-diene-3,17-dione.

The present invention requires a non-aromatic oxygenated acid with a $pK_\alpha$ of less than or equal to 1.0. Hydrogen fluoride pyridine reagent is not an oxygenated acid and it has a $pK_\alpha$ of greater than 1.0.

Dehydration of alcohols with acids is well known to those skilled in the art. The acid dehydration of tertiary alcohols is so well known that the mechanism has been worked out. The acid protonates the hydroxyl group. Upon leaving of the protonated hydroxyl group as water, the reactant is left as a carbonium ion. Loss of a proton from the carbonium ion takes place so as to form the thermodynamically most stable olefin. This acid dehydration of tertiary alcohols normally leads to the more substituted alkene and is known as an $E_1$-type reaction, see Basic Principles of Organic Chemistry, J. D. Roberts and M. C. Caserio, W. S. Benjamin, Inc., New York, 1964, pp. 313 and 396; and Mechanism and Structure in Organic Chemistry, E. S. Gould, Holt, Reinhart and Winston, New York, 1964, pp. 475 and 480. It is now clear that when two different olefins may result from a tertiary alcohol by an $E_1$ elimination reaction, the olefin bearing the larger number of alkyl substituents will predominate in the absence of complicating effects. This rule of organic chemistry is to well known that it is termed Saytzeff's Rule, see Gould, supra, p. 481.

Following Saytzeff's Rule acid dehydration of 9α-hydroxy steroids should yield predominately the corresponding $\Delta^8$-steroid and not the corresponding $\Delta^{9(11)}$-steriod. More particularly, acid dehydration of 9α-hydroxyandrostenedione (I) should produce predominantly androsta-4,8-diene-3,17-dione and not androsta4,9(11)-diene-3,17-dione (II).

The process of the present invention dehydrates 9α-hydroxyandrostenedione-type compounds (I) to the corresponding androsta-4,9(11)-diene-3,17-dione-type compounds (II) in very high yields with a ratio for androsta-4,9(11)-diene-3,17-dione (II) to androsta-4,8-diene-3,17-dione of greater than 98 to 2. This high yield and very high ratio is most surprising and unexpected in view of the prior art methods and the literature descriptions of the method of acid dehydration of tertiary alcohols and is highly advantageous from a commercial point of view.

BRIEF DESCRIPTION OF THE INVENTION

Disclosed is a process for the preparation of a steroid of the formula:

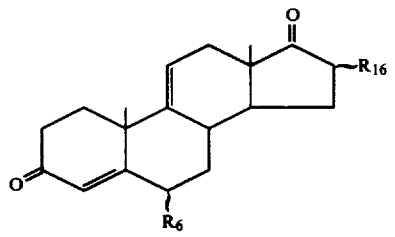

II which comprises reacting a 9α-hydroxy steroid of the formula:

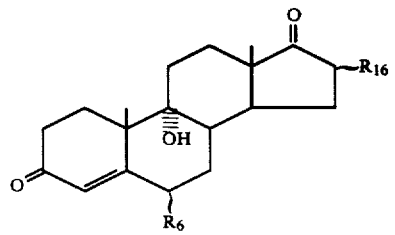

I where $R_6$, $R_{16}$ and ~ are defined below with a nonaromatic oxygenated acid with a $pK_a$ of less than or equal to 1.0.

The definitions and explanations below are for the terms as used throughout the entire patent application including both the specification and the claims.

$R_6$ is a hydrogen or fluorine atom or methyl group.

$R_{16}$ is a hydrogen atom or methyl group.

~ indicates that the $R_6$ and $R_{16}$ groups are in the α or β configuration.

$\Delta^{9(11)}$ refers to the double bond between carbon atoms 9 and 11 in the steroid.

All temperatures are in degrees Centigrade.

TLC refers to thin layer chromatography.

GC refers to gas chromatography.

UV refers to ultraviolet spectroscopy.

SSB refers to a mixture of isomeric hexanes.

p-TSA refers to p-toluenesulfonic acid (p-methylphenylsulfonic acid).

Chlorosulfonic acid refers to $ClSO_3H$.

Methanesulfonic acid refers to $CH_3SO_3H$.

Disclosed is a process for the preparation of androsta4,9(11)-diene-3,17-dione type compounds (II) which comprises reacting a 9α-hydroxy steroid (I) with chlorosulfonic acid.

Disclosed is a process for preparation of androsta4,9(11)-diene-3,17-dione type compounds (II) which comprises reacting a 9α-hydroxy steroid (I) with sulfuric acid.

[Also disclosed is a process for the preparation of a androsta-4,9(11)-diene-3,17-dione type compounds (II) which comprises reacting a 9α-hydroxy steroid (I) with phosphoric acid.]

Further disclosed is a process for the preparation of androsta-4,9(11)-diene-3,17-dione type compounds (II) which comprises reacting a 9α-hydroxy steroid (I) with methanesulfonic acid.

DETAILED DESCRIPTION OF THE INVENTION

The process of the present invention for preparation of an androsta-4,9(11)-diene-3,17-dione type compound (II) comprises dehydration of a 9α-hydroxy steriod (I) with a non-aromatic oxygenated acid with a $pK_a$ of less than or equal to 1.0.

The reactant for the process of the present invention is the 9α-hydroxy steroid of formula I:

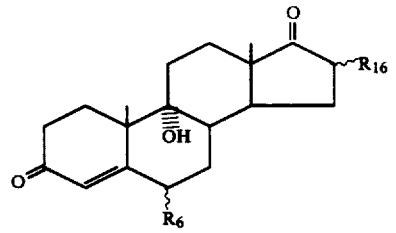

I $R_6$ is a hydrogen or fluorine atom or methyl group. $R_{16}$ is a hydrogen atom or methyl group. ~ indicates that the attachment of the $R_6$ and $R_{16}$ groups are in the α or β configuration.

The 9α-hydroxyandrostenediones within the scope of formula I are either known to those skilled in the art, or can readily be prepared by methods well known to those skilled in the art from readily available known compounds.

The acids of the present invention are non-aromatic. Therefore, acids such as benzoic, picric, 2,4-dinitrobenzoic, p-TSA, 1- and 2-naphthoic and naphthalenesulfonic acids are not within the scope of the present invention.

The acids of the present invention are oxygenated, i.e., contain the element oxygen. Therefore, acids such as hydrochloric, hydrobromic, hydrofluoric and hydrocyanic are not within the scope of the present invention.

The acids of the present invention have a $pK_a$ of less than or equal to 1.0. The $pK_a$ of an acid is defined as the negative logarithm (to the base 10) of the dissociation constant $K_a$, for the dissociation of the acid, HA.

$$HA = H^+ + A^-$$

$$Ka = ([H^+][A^-])[HA]$$

$$pK_a = -\log K_a$$

See The Condensed Chemical Dictionary, Eighth Edition, G. G. Hawley, Van Nostrand Reinhold Co., 1972, p. 698 and Physical Chemistry, Second Edition, F. Daniels and R. A. Alberty, John Wiley & Sons, Inc., 1961, p. 428–9.

The thermodynamic dissociation constant, $K_a$, is dependent on temperature and the solvent. See Daniels and Alberty, supra, p. 429. Therefore, in the present invention a $pK_a$ less than or equal to 1.0 refers to the $pK_a$ at 25° in distilled water.

It is preferred that the acids of the present invention be selected from the group consisting of chlorosulfonic, sulfuric, [phosphoric,] methanesulfonic, perchloric and trifluoroacetic. It is more preferred that the acid be selected from the group consisting of chlorosulfonic, sulfuric, phosphoric and methanesulfonic.

Chlorosulfonic acid must be used in a non-aqueous organic diluent. Suitable organic diluents include methylene chloride, chloroform, carbon tetrachloride, SSB, hexane, ethyl acetate, dichloroethane or mixtures thereof. The organic diluent is advantageous because upon crystallization most impurities are retained by the organic diluent providing the desired androsta-4,9(11)-diene-3,17-dione in very pure form. It is preferred that chlorosulfonic acid be present in 0.8–5 equivalents. It is more preferred it be present in 2–3 equivalents.

Chlorosulfonic acid reacts instantaneously with water. Therefore, some of the chlorosulfonic acid present will be utilized to dehydrate the organic diluent. During the dehydration reaction the 9α-hydroxy group and a hydrogen atom from $C_{11}$ are split off. Therefore, enough chlorosulfonic acid must be utilized to dehydrate the organic diluent, to react with the water generated by the dehydration reaction and to catalyze the dehydration reaction.

The reaction will proceed with as little as 0.8 equivalents of chlorosulfonic acid. As states previously, 2–3 equivalents of chlorosulfonic acid is more preferred. The reaction proceeds adequately even when 5 equivalents of chlorosulfonic acid are used. As is well known to those skilled in the art when smaller amounts of the acid (0.8–2 equivalents) are used the temperature must be increased and/or allow the reaction to proceed for a longer time. When larger amounts of acid (3–5 equivalents) are used the temperature may be decreased (−50° to 0°) to prevent destruction of the 9α-hydroxyandrostenedione (I) and/or androsta-4,9(11)-diene-3,17-dione (II). With 3–5 equivalents of chlorosulfonic acid the reaction time will be quite short, in the order of 10 minutes or less.

When practicing the present invention in an organic diluent the 9α-hydroxy steroid (I) is mixed with the organic diluent. Chlorosulfonic acid is then added, either in pure form or dissolved in an organic diluent, to the steroid mixture with continuous stirring, mixing or agitating. The temperature is maintained in the range −50° to 20°, preferably about −20° to 0°. The time for the reaction to reach completion is very short and varies from a few minutes to about one hour and is monitored by TLC as described below. The reaction is usually complete in 5–10 minutes. Upon completion of the reaction as measured by TLC, water is added slowly with cooling. The two-phase system is worked up by methods well known to those skilled in the art. The organic phase may be washed with a dilute base such as aqueous sodium bicarbonate (10%), potassium carbonate (20%), or sodium or potassium hydroxide (2%) and then with water. The aqueous washes are back extracted with an organic diluent which is then added to the organic phase. The organic phase is dried and concentrated under vacuum. An organic diluent such as ethyl acetate, methanol, heptane, hexane, or cyclohexane is added and the mixture is cooled. The resulting crystals are filtered, washed with the organic diluent and dried.

The reaction as described above is monitored by TLC. As the reaction proceeds to completion the more polar 9α-hydroxy steroid (I) disappears leaving a less polar spot (TLC) which corresponds to the $\Delta^{9(11)}$-steroid (II). Upon dehydration of a 9α-hydroxy steroid (I) the $\Delta^8$ and $\Delta^{9(11)}$-steroids are both products which may result, either singly or in a mixture. Both the $\Delta^8$ and $\Delta^{9(11)}$-steroids have very similar or identical Rf values in most solvent systems. Therefore, to determine whether the resulting less polar product is androsta-4,9(11)-diene-3,17-dione, androsta-4,8-diene-3,17-dione, or a mixture of these compounds, a sample of the reaction mixture should be analyzed by gas chromatography (GC). It has been found that the $\Delta^{9(11)}$- and $\Delta^8$-isomeric steroids can be readily separated and the amount of the $\Delta^{9(11)}$-isomer readily determined by GC.

The GC assay utilizes a 3% OV-17 column which is 180 cm.×3 mm. The column temperature is 250°. Under these conditions androsta-4,8-diene-3,17-dione and androsta-4,9(11)-diene-3,17-dione are readily separable, the retention time of androsta-4,8-diene-3,17-dione is less than androsta-4,9(11)-diene-3,17-dione. This assay procedure provides a qualitative assay as to which isomeric olefinic steroid is present and a quantitative assay of the relative amounts of each of the isomers when both are present.

Other non-aromatic oxygenated acids with a $pK_a$ of less than or equal to 1.0 also readily effectuate the dehydration of 9α-hydroxyandrostenedione (I) to androsta-4,9(11)-diene-3,17-dione (II) in very high yields with a androsta-4,9(11)-diene-3,17-dione/androsta-4,8-diene-3,17-dione ratio of greater than 98 to 2. These acids are usually used with a small amount of water (1–30%) present. However, acids such as sulfuric, [phosphoric,] methanesulfonic and trifluoroacetic may be used without any water (100% acid).

The preferred concentration of the preferred acids of the present invention are sulfuric, 60–100%; [phosphoric, 70–100%;] methanesulfonic, 70–100%; perchloric, 5–70%; and trifluoroacetic, 70–100%. A more preferred range for the concentration of these acids is sulfuric, 70–96%; [phosphoric, 80–90%;] methanesulfonic, 80–90%, perchloric, 20–40%; and trifluoroacetic, 75–95%.

The above concentrations of the acids are specified in percent (%) as determined by weight of acid used/weight of acid used plus weight of water present (w/w).

Various combinations of the acids of the present invention may be used. For example a mixture of 50 g. sulfuric acid with 50 g. of phosphoric acid is only 50% acid with respect to each acid, however as would be easily recognized by one skilled in the art the actual acid strength of such a mixture is 100%, 0% water and is equivalent to 100% of either of the acids individually.

Diluents other than water may be used. For example, formic or acetic acid may be used as a diluent for the acids of the present invention.

Alternatively, the process of the present invention may be practiced in two-phase aqueous-organic system with the exception of chlorosulfonic acid. The organic diluents are the same as those previously described for chlorosulfonic acid. The acid-water phase of the two-phase system may comprise 10–99 percent of the two-phase system.

When the concentration of the aqueous acids is less than the preferred range, high yields are still obtained. More importantly even if the yield decreases somewhat, the ratio of androsta-4,9(11)-diene-3,17-dione to androsta-4,8-diene-3,17 -dione remains greater than 98 to 2 which is of great commercial importance and most unexpected. With concentrations of the aqueous acids less than the preferred ranges the reaction temperature and time are increased as is well known to those skilled in the art. The aqueous acid concentration ranges are preferred because it permits the use of lower reaction temperatures (−50° to 50°, preferably 0°–25°) and shorter reaction times, usually 1–10 hours. The reaction is monitored by TLC as described above.

Examples 12–15 disclose the use of methanesulfonic acid. Examples 12 and 13 disclose the use of methanesulfonic acid in the preferred range, obtaining yields of 94.2% and 95.6%, respectively. Examples 14 and 15 disclose the use of methanesulfonic acid at a concentration less than the preferred range. Lower temperatures and longer reaction times would have increased the yields. Even though the yields were reduced to 55.7% and 75.9%, respectively, it is surprising and unexpected that the ratio of androsta-4,9(11)-diene-3,17-dione to androsta-4,8-diene-3,17-dione is greater than 99 to 1.

The water produced by the dehydration process of the present invention dilutes the acid concentration and is another reason why it is preferable to use the preferred acid concentrations.

Upon completion of the reaction is measured by TLC the reaction mixture is quenched with water and worked up as is well known to those skilled in the art.

EXAMPLES

The invention may be more fully understood from the following examples which are illustrative of the process and compounds of the present invention but are not to be construed as limiting.

EXAMPLE 1

Dehydration of 9α-hydroxyandrostenedione (I) to androsta-4,9(11)-diene-3,17-dione (II) with chlorosulfonic acid (Formulas I and II; $R_6$ and $R_{16}$ are hydrogen)

9α-Hydroxyandrostenedione (U.S. Pat. No. 3,065,146, Example 6, 5.00 g.) is dissolved in methylene chloride (50 ml.) and cooled to 0°–5°. A solution of chlorosulfonic acid (1.3 ml.) in methylene chloride (10 ml.) is slowly added to the steroid mixture. The mixture is stirred at 0°–5° for 1 hour. A second solution of chlorosulfonic acid (1.3 ml.) in methylene chloride (10 ml.) is added to the steroid mixture. After 3 minutes of stirring the reaction is complete as measured by TLC (ethylacetate: benzene, 1:1).

Water (70 ml.) is added over a 5 minutes period maintaining the temperature 3°–18°. The two-phase system is separated and the aqueous phase is back extracted with methylene chloride (25 ml.) which is combined with the steroid mixture and washed with water (50 ml.). A saturated sodium chloride solution (5 ml.) is added to break the emulsion. The organic phase is concentrated to about 30 ml. Heptane (70 ml.) is added and the mixture is concentrated to about 30 ml. Heptane (70 ml.) is added and the mixture is concentrated with heat (87°). After the solids begin to precipitate the mixture is cooled to 0°–5°. The solids are collected by filtration, washed with a minimum amount of heptane and dried overnight at 70° to give 4.00 g. (80.0% weight yield, 85.0% chemical yield) of material which by GC (3% OV-17, 180 cm.×3 mm at 250°) is found to be 100% androsta-4,9(11)-diene-3,17-dione; m.p. 194°–201°; $[\alpha]_D+221°$ (chloroform); UV (methanol) $\lambda_{max}=240$ nm ($\epsilon=16{,}800$).

EXAMPLE 2

Dehydration of 9α-hydroxyandrostenedione (I) to androsta-4,9(11)-diene-3,17-dione (II) with chlorosulfonic acid (Formulas I and II: $R_6$ and $R_{16}$ are hydrogen)

9α-Hydroxyandrostenedione (10.00 g.) is dissolved in methylene chloride (100 ml.) and cooled to 0°–5°. Chlorosulfonic acid (5 ml.) is added dropwise and the mixture stirred to 0.5 hour at 0°–5°. Water (50 ml.) is added dropwise while the temperature rises to 23°. The mixture is stirred for 5 minutes and the phases separated. The organic phase is washed with an aqueous sodium bicarbonate solution (10%, 25 ml.) and water (50 ml.) containing 10 ml. of a saturated sodium chloride solution. Each of the aqueous washes is back extracted with the same methylene chloride (25 ml.) which is then added to the organic phase. The organic phase is concentrated to approximately 50 ml. Heptane (100 ml.) is added and the mixture concentrated to approximately 50 ml. with the temperature reaching a maximum of about 35°. The mixture is cooled to 0°–5°, Stirred 0.5 hour, the solids are collected by filtration, under vacuum at 55° to give androsta-4,9(11)-diene-3,17-dione, 8.95 g. (89.5% weight yield, 95.0% chemical yield). GC (Example 1) shows 99% androsta-4,9(11)-diene-3,17-dione.

EXAMPLE 3

Dehydration of 9α-hydroxyandrostenedione (I) to androsta-4,9(11)-diene-3,17-dione (II) with chlorosulfonic acid (Formulas I and II: $R_6$ and $R_{16}$ are hydrogen)

9α-Hydroxyandrostenedione (5.00 g.) is dissolved in methylene chloride (50 ml.) and cooled to 0°–5°. A solution of chlorosulfonic acid (2.5 ml.) in methylene chloride (10 ml.) is added slowly over a period of 4 minutes. At the end of the addition TLC shows the reaction is completed. Water (60 ml.) is added to the reaction mixture keeping the temperature at 3°–15°. The mixture is stirred for 2 minutes and heptane (135 ml.) is added. The organic phase is separated and washed twice with water (30 ml. each time). The organic phase is concentrated with heat to about 30 ml. with crystals forming as the solution cools. The mixture is cooled to 0°–5°, filtered, washed with a minimum amount of heptane, and dried at 70° to give androsta-4,9(11)-diene-3,17-dione; 4.45 g. (89.0% weight yield, 94.7% chemical yield), m.p., 195.5°–202°; $[\alpha]_D+220°$ (chloroform); UV (methanol) $\lambda_{max}=240$ nm ($\epsilon=16{,}300$).

EXAMPLE 4

Dehydration of 9α-hydroxyandrostenedione (I) to androsta-4,9(11)-diene-3,17-dione (II) with chlorosulfonic acid (Formulas I and II: $R_6$ and $R_{16}$ are hydrogen)

Following the procedure of Example 2 but making noncritical variations 9α-hydroxyandrostenedione (10.00 g.) is reacted with chlorosulfonic acid to give androsta-4,9(11)-diene-3,17-dione, 9.01 g. (90.1% weight yield, 95.7% chemical yield).

EXAMPLE 5

Dehydration of 9α-hydroxyandrostenedione (I) to androsta-4,9(11)-diene-3,17-dione (II) with chlorosulfonic acid (Formulas I and II: $R_6$ and $R_{16}$ are hydrogen)

9α-Hydroxyandrostenedione (192.00 g.) is dissolved in methylene chloride (1440 ml.) and cooled to −20° at which point the steroid is no longer in solution. Chlorosulfonic acid (115.6 ml.) is added over a period of 1 hour.

The mixture is stirred at −15° to −20° C. for 1.5 hours. Water (480 ml.) is added with the temperature rising from −15° to 27°. The mixture is stirred approximately 5 minutes and the phases separated. The aqueous phase is extracted with methylene chloride (250 ml.) with an emulsion resulting. A saturated sodium chloride solution (150 ml.) is added to break the emulsion. The aqueous phase is discarded and the methylene chloride extract retained.

The original organic phase (1440 ml.) is neutralized with an aqueous sodium bicarbonate solution (10%, 480 ml.). A second portion of aqueous sodium bicarbonate solution (10%, 480 ml.) is also added, the final pH is about 8.2 The two-phase system is permitted to stand overnight to obtain better separation of the phases. The aqueous phase is extracted with the methylene chloride extract resulting from extraction of the original aqueous phase. Following extraction of the 960 ml. sodium bicarbonate wash, the methylene chloride extract is combined with the original organic phase.

The combined organic phases are extracted with aqueous sodium bicarbonate. This aqueous sodium bicarbonate extract is extracted with methylene chloride which upon concentration yields 1.85 g. of androsta-4,9(11)-diene-3,17-dione.

The combined organic phases are concentrated under vacuum to 770 ml. with a bath temperature of 58° and a pot temperature of 23°. Heptane (960 ml.) is added and the mixture is again concentrated to a final volume of approximately 700 ml. The mixture is cooled to about 10° and the solids are collected by filtration. The crystalline material is washed twice with heptane (100 ml. each time). The solids are dried under vacuum at 55° to give androsta-4,9(11)-diene-3,17-dione, 170.85 g., (89.0% weight yield, 94.5% chemical yield). Upon analysis by GC (Example 1) the material is found to be approximately 99% androsta-4,9(11)-diene-3,17-dione.

EXAMPLE 6

Dehydration of 9α-hydroxyandrostenedione (I) to androsta-4,9(11)-diene-3,17-dione (II) with chlorosulfonic acid (Formulas I and II: $R_6$ and $R_{16}$ are hydrogen)

9α-Hydroxyandrostenedione (20.00 g.) is dissolved in methylene chloride (150 ml.) and cooled to −19°. Chlorosulfonic acid (10 ml.) is added while maintaining the temperature at less than or equal to −9°. After only a few minutes the reaction is shown to be nearly complete as measured by TLC. Additional chlorosulfonic acid (1 ml.) is added. Water (50 ml.) is added to the reaction mixture with the temperature rising from −18° to −1°. The phases are separated and the aqueous phase is extracted with methylene chloride (125 ml.). The organic phase is washed with aqueous sodium bicarbonate solution (10%, 50 ml.). The aqueous phases are combined and back extracted with methylene chloride. The organic phases are combined and concentrated under vacuum to approximately 80 ml. at a temperature of about 20°-23°. Heptane (100 ml.) is added and the mixture stirred for approximately 4 minute at approximately 19°. The mixture is concentrated under vacuum to approximately 100 ml. at a temperature of about 25°-30°. Heptane (50 ml.) is again added and the mixture again concentrated to approximately 100 ml. The mixture is cooled to 25° and stirred for 15 minutes, filtered, and the crystalline material washed with heptane (25 ml.) and dried under vacuum at 50° to give androsta-4,9(11)-diene-3,17-dione, 17.96 g. (89.8% weight yield, 95.3 % chemical yield); m.p. 197.5°-203.5°; $[\alpha]_D+220°$ (chloroform); UV (methanol)$\lambda_{max}=240$ nm ($\epsilon=16,200$).

EXAMPLE 7

Dehydration of 9α-hydroxyandrostenedione (I) to androsta-4,9(11)diene-3,17-dione (II) with chlorosulfonic acid (Formulas I and II: $R_6$ and $R_{16}$ are hydrogen)

Following the general procedure of Example 6 but making non-critical variations, 9α-hydroxyandrostenedione (20.00 g.) is reacted with chlorosulfonic acid (10 ml.) at a reaction temperature of 1°-11°. Upon workup the reaction gives androsta-4,9(11)-diene-3,17-dione, 17.94 g., (89.7% weight yield, 95.2% chemical yield); m.p. 202°-204.5°; $[\alpha]_D+217°$ (chloroform); UV (methanol($\lambda_{max}=240$ nm ($\epsilon=16,300$).

EXAMPLE 8

Dehydration of 9α-hydroxyandrostenedione (I) to androsta-4,9(11)-diene-3,17-dione (II) with chlorosulfonic acid (Formulas I and II: $R_6$ and $R_{16}$ are hydrogen)

Following the general procedure of Example 6 but making non-critical variations, 9α-hydroxyandrostenedione (20.00 g.) is reacted with chlorosulfonic acid (10 ml.) at a temperature of 20°-27° for 17 minutes. Upon workup the reaction gives androsta-4,9(11)-diene-3,17-dione, 15.9 l g., (79.5% weight yield, 84.4 % chemical yield); m.p. 200.5°-204°; $[\alpha]_D+218°$ (chloroform); UV (methanol)$\lambda_{max}=240$ nm ($\epsilon=15,200$).

EXAMPLE 9

Dehydration of 9α-hydroxyandrostenedione (I) to androsta-4,9(11)-diene-3,17-dione (II) with sulfuric acid (Formulas I and II: $R_6$ and $R_{16}$ are hydrogen)

9α-Hydroxyandrostenedione (9.07 g.) is added to aqueous sulfuric acid (22.5 ml. of 70%; 3 parts water and 7 parts sulfuric acid). The resulting slurry is stirred at 23°-25° until the reaction is complete as measured by TLC(ethyl acetate:hexane, 60:40). When complete the reaction mixture is cooled (10°) and added dropwise to ice-water (800 ml.) with rapid stirring. The resulting slurry is stirred overnight, filtered and the solids washed with water (500 ml.), sodium bicarbonate solution (10%, 500 ml.) and water (500 ml.). The solids are air-dried to give androsta-4,9(11)-diene-3,17-dione, 8.31 g. (97.4% chemical yield); m.p. 196°201°; $[\alpha]_D+219°$ (chloroform); UV (methanol)$\lambda_{max}=240$ nm ($\epsilon=16,500$). GC (Example 1) shows an androsta-4,9(11)-diene-3,17-dione/androsta-4,8-diene-3,17-dione ratio of greater than 99 to 1.

EXAMPLE 10

Dehydration of 9α-hydroxyandrostenedione (I) to androsta-4,9(11)-diene-3,17-dione (II) with phosphoric acid (Formulas I and II: $R_6$ and $R_{16}$ are hydrogen)

9α-Hydroxyandrostenedione (280 mg.; 302 mg. of 92.7% purity) is added to phosphoric acid (85%, 5 ml.) and stirred at 35°-48° for 7.5 hours. Water (10 ml.) is then added, the mixture stirred and filtered. The solids are air-dried at 25° for 10 hours to give androsta-4,9(11)-diene-3,17-dione, 254 mg. (90.7% weight yield, 96.2% chemical yield); m.p. 197°-201°. GC (Example 1) shows an androsta-4,9(11)-diene-3,17-dione/androsta-4,8-diene-3,17-dione ratio greater than 99 to 1.

EXAMPLE 11

Dehydration of 9α-hydroxyandrostenedione (I) to androsta-4,9(11)-diene-3,17-dione (II) with phosphoric acid (Formulas I and II: $R_6$ and $R_{16}$ are hydrogen)

9α-Hydroxyandrostenedione (9.06 g.) is added to phosphoric acid (85%, 25 ml.) and stirred at 45°-55° for 24 hours. Water (75 ml.) is added, the mixture stirred for 2 hours and the solids are collected by filtration. The solids are washed with water (200 ml.) and air-dried to give androsta-4,9(11)-diene-3,17-dione, 8.11 g., (95.1% chemical yield); m.p. 193°-195°.

EXAMPLE 12

Dehydration of 9α-hydroxyandristenedione (I) to androsta-4,9(11)-diene-317-dione (II) with methanesulfonic acid (Formulas I and II: $R_6$ and $R_{16}$ are hydrogen)

9α-Hydroxyandrostenedione (0.302 g.) is mixed with water (0.60 ml.) and methanesulfonic acid (2.40 ml.) at 35° with stirring under nitrogen. After 5 hours at 31°-39° the reaction is quenched by adding water (20 ml.). The temperature is increased to 80° and then decreased slowly to 5°, and after 45 minutes the slurry is filtered to collect the solids. The solids are washed thoroughly with water and air-dried to give androsta-4,9(11)-diane-3,17-dione, 0.268 g. (94.2% chemical yield), m.p. 193°-198°.

The above solids are dissolved in a mixture of methanol:methylene chloride, 8:1 (9 ml.). The mixture is filtered and the filtrate concentrated at ordinary pressure to about 5 ml. Water (4 ml.) at 60° is added and the mixture stirred for about 1 hour while cooling to about 30°. The mixture is cooled to 0° and permited to stand for 1 hour, then filtered, the solids washed with methanol:water, 1:1 (2 ml.) and air-dried to give androsta-4,9(11)-diene-3,17-dione, 0.248 g. (87.2% chemical yield); m.p. 198.5°-201°.

EXAMPLE 13

Dehydration of 9α-hydroxyandrostenedione (I) to androsta-4,9(11)-diene-3,17-dione (II) with methanesulfonic acid (Formulas I and II: $R_6$ and $R_{16}$ are hydrogen)

9α-Hydroxyandrostenedione (.302 g.) is stirred in methanesulfonic acid (3.0 ml.) at 25°. After 80 minutes the reaction is quenched by addition of water (15 ml.). The solids are stirred for 2 hours at 35°, collected, air-dried overnight to give androsta-4,9(11)-diene-3,17-dione, 0.272 g. (95.6% chemical yield).

EXAMPLE 14

Dehydration of 9α-hydroxyandrostenedione (I) to androsta-4,9(11)-diene-3,17-dione (II) with methanesulfonic acid (Formulas I and II: $R_6$ and $R_{16}$ are hydrogen)

9α-Hydroxyandrostenedione (280 mg.; 302 mg. of 92.7% purity) is added to a solution of water (3 ml.) and methanesulfonic acid (1 ml.) and stirred at 22° for 2 hours. Additional methanesulfonic acid (1 ml.) is added and stirred for 6 hours with heating to 68°. The reaction mixture is quenched by addition of water (20 ml.) and benzene (20 ml.). Work-up gives androsta-4,9(11)-diene-3,17-dione, 147 mg. (55.7% chemical yield); m.p. 186°-194°. GC (Example 1) shows an androsta-4,9(11)-diene-3,17-dione/androsta-4,8-diene-3,17-dione ratio of greater than 99 to 1.

EXAMPLE 15

Dehydration of 9α-hydroxyandrostenedione (I) to androsta-4,9(11)-diene-3,17-dione (II) with methanesulfonic acid (Formulas I and II: $R_6$ and $R_{16}$ are hydrogen)

9α-Hydroxyandrostenedione (302 mg.) is added to a solution of water (2.5 ml.) in methanesulfonic acid (2.5 ml.) and heated to 100°. The mixture is slowly cooled over a period of 2 hours to 60°. Water (3 ml.) is added and the reaction mixture seeded. Work-up gives androsta-4,9(11)-diene-3,17-dione, 216 mg. (75.9% chemical yield - crude material), m.p. 170°-175°. Upon recrystallization a m.p. of 190°-194° is obtained.

EXAMPLE 16

Dehydration of 9α-hydroxyandrostenedione (I) to androsta-4,9(11)-diene-3,17-dione (II) with perchloric acid (Formulas I and II: $R_6$ and $R_{16}$ are hydrogen)

9α-Hydroxyandrostenedione (302 mg.) is added to water (5 ml.) with stirring at 33°. Perchloric acid (1.50 ml. of 70%) is added and the temperature is slowly increased to 78°. The mixture is cooled to 54° and perchloric acid (0.50 ml. of 70%) is added. After 28 hours TLC (ethyl acetate:hexane, 60:40) shows 90:95% androsta-4,9(11)-diene-3,17-dione and about 5% starting material. The reaction is continued for an additional 38 hours producing androsta-4,9(11)-diene-3,17-dione, 198 mg. (69.6% chemical yield).

EXAMPLE 17

Dehydration of 9α-hydroxyandrostenedione (I) to androsta-4,9(11)-diene-3,17-dione (II) with a mixture of sulfuric and phosphoric acid (Formulas I and II: $R_6$ and $R_{16}$ are hydrogen)

Following the procedure of Example 9 but substituting sulfuric acid (15 ml. of 90% sulfuric acid) and phosphoric acid (15 ml. of 85% phosphoric acid) for the 22.5 ml. of 70% sulfuric acid, androsta-4,9(11)-diene-3,17-dione is obtained.

We claim:

1. A process for the preparation of a steroid of the formula:

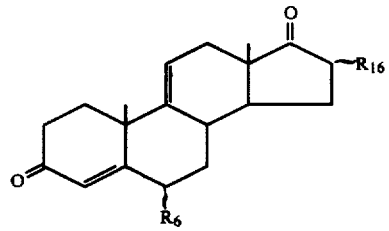

II where $R_6$ is a hydrogen or fluorine atom, or a methyl group; $R_{16}$ is a hydrogen atom or methyl group and where ~ indicates that the attachment of the $R_6$ and $R_{16}$ groups are in the α or β configuration which comprises reacting a 9α-hydroxy steroid of the formula:

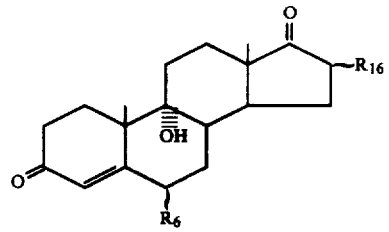

I where $R_6$, $R_{16}$, and ~ are defined above with a nonaromatic oxygenated acid with a $pK_a$ of less than or equal to 1.0.

2. A process according to claim 1 where the acid is selected from the group consisting of chlorosulfonic, sulfuric, [phosphoric,] methanesulfonic, perchloric and trifluoroacetic.

3. A process according to claim 2 where 0.8-5 equivalents of chlorosulfonic acid is present, sulfuric acid is present at a concentration of 60-100%, [phosphoric acid and] methanesulfonic acid are present at a concentration of 70–100%, perchloric acid is present at a concentration of 5–70% and trifluoroacetic acid is present at a concentration of 70–100%.

4. A process according to claim 3 where 2–3 equivalents of chlorosulfonic acid is present, sulfuric acid is present at a concentration of 70–96%, [phosphoric acid and] methane-sulfonic acid are present at a concentration of 80–90%, perchloric acid is present at a concentration of 20–40%, and trifluoroacetic acid is present at a concentration of 75–95%.

5. A process according to claim 4 where the steroid (I) is 9α-hydroxyandrostenedione.

6. A process according to claim 2 where the acid is chlorosulfonic acid.

7. A process according to claim 6 where 0.8–5 equivalents of chlorosulfonic acid are present.

8. A process according to claim 2 where the acid is sulfuric acid.

9. A process according to claim 8 where the sulfuric acid is present at a concentration of 60–100%.

[10. A process according to claim 2 where the acid is phosphoric acid.]

[11. A process according to claim 10 where the phosphoric acid is present at a concentration of 70–100%.]

12. A process according to claim 2 where the acid is methanesulfonic acid.

13. A process according to claim 12 where the methanesulfonic acid is present at a concentration of 70–100%.

14. A process for the preparation of androsta-4,9(11)-diene-3,17-dione which comprises reacting 9α-hydroxyandrostenedione with chlorosulfonic acid.

15. A process according to claim 14 where 0.8–5 equivalents of chlorosulfonic acid are present.

16. A process according to claim 15 where 2–3 equivalents of chlorosulfonic acid are present.

17. A process for the preparation of androsta-4,9(11)-diene-3,17-dione which comprises reacting 9α-hydroxyandrostenedione with sulfuric acid.

18. A process according to claim 17 where the sulfuric acid is present at a concentration of 60–100%.

19. A process according to claim 18 where the sulfuric acid is present at a concentration of 70–96%.

20. A process for the preparation of androsta-4,9(11)-diene-3,17-dione which comprises reacting 9α-hydroxyandrostenedione with phosphoric acid.

21. A process according to claim 20 where the phosphoric acid is present at a concentration of 70–100%.

22. A process according to claim 21 where the phosphoric acid is present at a concentration of 80–90%.

23. A process for the preparation of androsta-4,9(11)-diene-3,17-dione which comprises reacting 9α-hydroxyandrostenedione with methanesulfonic acid.

24. A process according to claim 23 where the methanesulfonic acid is present at a concentration of 70–100%.

25. A process according to claim 24 where the methanesulfonic acid is present at a concentration of 80–90%.

* * * * *